United States Patent [19]
Bolser

[11] Patent Number: 5,967,971
[45] Date of Patent: Oct. 19, 1999

[54] SURGICAL INSTRUMENT

[76] Inventor: Jeffrey William Bolser, 478 Carol Dr., Vadnais Heights, Minn. 55127

[21] Appl. No.: 09/060,021

[22] Filed: Apr. 14, 1998

[51] Int. Cl.$^6$ .................................................. A61B 17/00
[52] U.S. Cl. ........................................... 600/211; 600/245
[58] Field of Search ................................... 600/201, 212, 600/210, 235, 245, 199, 211, 241

[56] References Cited

U.S. PATENT DOCUMENTS

| | | | |
|---|---|---|---|
| 339,754 | 4/1886 | Foote | 600/241 |
| 2,296,793 | 9/1942 | Kirschbaum | 600/245 X |
| 2,690,745 | 10/1954 | Govan | 600/241 |
| 4,337,763 | 7/1982 | Petrassevich | 600/245 X |
| 4,344,419 | 8/1982 | Burgin | 600/241 X |

FOREIGN PATENT DOCUMENTS 723178  7/1942  Germany ............................. 600/241

*Primary Examiner*—Jeffrey A. Smith
*Attorney, Agent, or Firm*—Beck & Tysver, P.L.L.P; Robert C. Beck

[57] ABSTRACT

Surgical instrument, particularly a surgical retractor, for use in harvesting saphenous veins for use in coronary bypass operations. The retractor includes a handle, a retractor blade member including first and second limbs which define a view area axis, and a light source coupled to the retractor blade member for directing light away from the handle and away from the view area. The retractor may be inserted into a surgical wound to illuminate the surgical field. In use, the surgical retractor may be manipulated by a physician and can be used to expose sections of the vein and to facilitate blunt dissection along the length of the vein.

7 Claims, 1 Drawing Sheet

SURGICAL INSTRUMENT

FIELD OF THE INVENTION

The present invention relates generally to surgical instruments and more particularly to a surgical retractor well suited to harvesting saphenous veins for use in coronary bypass operations.

BACKGROUND OF THE INVENTION

Harvesting segments of the saphenous vein from the leg is a surgical procedure associated with coronary artery surgery. In general, segments of the patient's saphenous vein are removed, divided and repositioned in the coronary arterial system to improve coronary blood flow.

Early harvesting techniques involved conventional surgical cut down and open dissection of the leg to harvest the vein. In general less invasive procedures are preferred and several surgical devices have been developed to facilitate this procedure. See for example the "Mini Harvest" system manufactured by U.S. Surgical Corp. and the "VasoView" system manufactured by Origin as well as U.S. Pat. No. 5,667,480 to Knight et al. In general these systems are relatively complex and cumbersome in use although they are preferred over open dissection.

SUMMARY

In contrast to the prior art, the surgical retractor of the present invention is an easily manipulated illuminated device for insertion into the surgical wound to illuminate the surgical field. In use the device is manipulated by the physician and can be used to expose sections of the vein and it may be used to facilitate blunt dissection along the length of the vein. In operation the device can be used to simultaneously retract tissue and illuminate the surgical field at the same location. The illustrated embodiments of the device include a light source located near the distal tip of the retractor with an integral or remote power source of the light source.

BRIEF DESCRIPTION OF THE DRAWINGS

Throughout the several views of the drawing identical reference numerals refer to equivalent structural elements, wherein.

DETAILED DESCRIPTION

Figure 1:
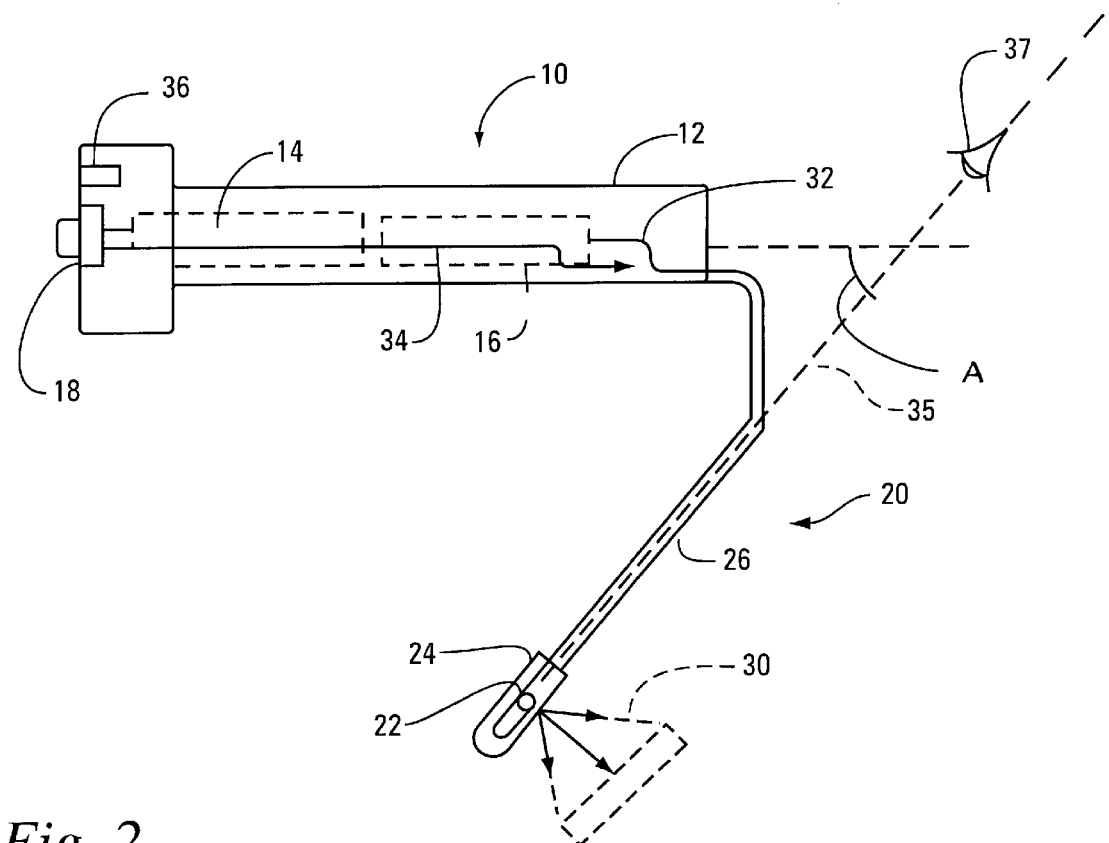
FIG. 1 is an illustrative view of the surgical retractor.

FIG. 1 shows a side view of an embodiment of the surgical instrument 10. A handle 12 is provided to receive the hand of the physician. A power source is provided and is illustrated by a pair of batteries illustrated in the figure by battery 14 and battery 16 which may be located inside of the handle 12. In this embodiment the proximal end of the handle 12 includes a switch assembly 18 which can be used to turn on the light source 22 or lamp.

A retractor blade 20 is anchored at the distal end of the handle 12. In general this retractor blade lies in a single plane and bends "away" from the handle 12. Near the distal tip of the retractor blade 20 is a lamp 22 or other source of illumination. In the embodiment shown in the drawing a single incandescent bulb is shown mounted on a web 24 spanning the distance between the first limb 26 and the second limb 28 of the retractor blade 20. In general it is best to mount the bulb such that the cone of illumination 30 is directed away from the handle 12. In use this illumination source directs light into the surgical field surrounding and defined by the distal tip of the retractor blade.

Figure 2:
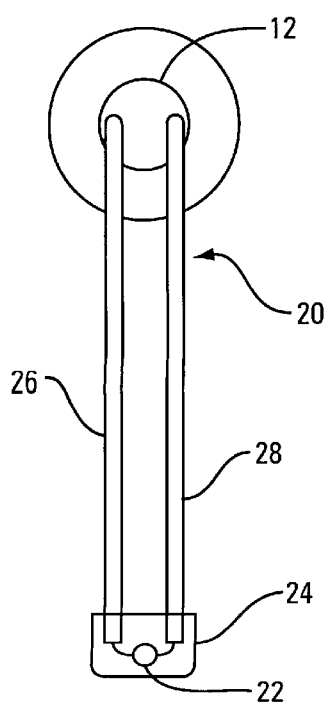
FIG. 2 is an illustrative view of the surgical retractor.

FIG. 2 shows an end view of the surgical instrument 10. In this view the two members 26 and 28 can been seen forming conductors for the light source 22. The web 24 can been seen spanning the distance between the two members. In general the web 24 is formed from a plastic material and the web adds mechanical strength to support the two members 26 and 28. The circuit to the power source is completed by suitable wiring 32 which couples the member 26 conductor to a battery 16. A complimentary wire 34 couples member 28 to the switch assembly 18.

The user with line of sight along line 35 from eye position 37 observes the surgical field between the two limbs 26 and limb 28. The line 35 forms an axis which lies in the plane defined by the two limb members 26 and 28.

Although a preferred embodiment of the instrument has been shown there are a number of variations that should considered within the scope of the claims. For, example the members 26 and 28 are shown as solid wire forms but alternate cross section forms are practical including square and rectangular shapes. However or tubular shape may be used as well. Although the inclusion of the power source in the handle is preferred for disposable versions of the device it should be clear that a remote power supply could be coupled to the handle via connector 36 to power the light source 22 from a remote supply (not shown). In a similar fashion the switch may take any conventional form or may be integrated into a remote power pack. The "bend" of the retractor blade 20 is acute with respect to the handle as indicated by angle A but other angular relationships are operable as well. For example the handle could be a reusable element with removable and disposable retractor blades temporally attached or coupled to the handle. The use of the members 26 and 28 as the conductors is preferred but separate wires may be used to deliver power to the light source 22.

What is claimed is:

1. A surgical instrument comprising:

a handle having a distal end and a proximal end;

a retractor blade member including a first limb and a second limb said member for insertion into a surgical wound, said retractor blade attached to said distal end of said handle, said retractor blade member extending in a direction away from said handle, whereby a view area axis is defined between said first and second limbs substantially parallel to the plane defined by said first and second limbs;

a light source coupled to said retractor blade for directing light away from said handle and away from said view area;

at least one conductor for coupling power to said retractor blade;

said light source coupled to said retractor blade.

2. The instrument of claim 1 further comprising:

a power source coupled to said handle.

3. The instrument of claim 1 further comprising:

a switch coupled to said handle for controlling said light source.

4. The instrument of claim 1 further comprising:

one or more batteries located within said handle forming a power source for said light source.

5. The instrument of claim 1 wherein said retractor blade comprises:
- a first electrically conductive member forming a first limb;
- a second electrically conductive member forming a second limb;
- said first and second members electrically isolated from each other and each coupled to said light source for conducting power to said light source.

6. The instrument of claim 5 further comprising:
- web coupled to said retractor blade for positioning said light source.

7. The instrument of claim 1 further comprising:
- a remote power source for connection to said handle, for powering said light source.

* * * * *